United States Patent
Ohsono et al.

(10) Patent No.: US 7,684,449 B2
(45) Date of Patent: Mar. 23, 2010

(54) OPTICAL FIBER FOR FIBER LASER DEVICE AND FIBER LASER DEVICE USING SAME

(75) Inventors: Kazumasa Ohsono, Hitachi (JP); Akihito Hongo, Hitachi (JP); Seiji Kojima, Hitachi (JP); Bing Yao, Hitachi (JP)

(73) Assignee: Hitachi Cable, Ltd., Tokyo (JP)

( * ) Notice: Subject to any disclaimer, the term of this patent is extended or adjusted under 35 U.S.C. 154(b) by 14 days.

(21) Appl. No.: 11/987,668

(22) Filed: Dec. 3, 2007

(65) Prior Publication Data

US 2008/0192778 A1   Aug. 14, 2008

(30) Foreign Application Priority Data

Dec. 4, 2006   (JP) .............................. 2006-327359

(51) Int. Cl.
H01S 3/30   (2006.01)
(52) U.S. Cl. ............................................. 372/6; 372/64
(58) Field of Classification Search ...................... 372/6, 372/64
See application file for complete search history.

(56) References Cited

U.S. PATENT DOCUMENTS

| | | |
|---|---|---|
| 6,404,966 B1 | 6/2002 | Kawanishi et al. |
| 6,985,661 B1 | 1/2006 | Russell et al. |
| 7,190,862 B1 * | 3/2007 | Peterson ...................... 385/41 |
| 2004/0184753 A1 | 9/2004 | Teramura |
| 2005/0105867 A1 * | 5/2005 | Koch et al. .................. 385/125 |
| 2008/0273852 A1 * | 11/2008 | Parker et al. ................ 385/128 |

FOREIGN PATENT DOCUMENTS

| | | |
|---|---|---|
| JP | 56-12602 | 2/1981 |
| JP | 59-68701 | 4/1984 |
| JP | 2000-035521 | 2/2000 |
| JP | 2000-35521 | 2/2000 |
| JP | 2000-131570 | 5/2000 |
| JP | 2002-350694 | 12/2002 |
| JP | 2002-541507 | 12/2002 |
| JP | 2004-219244 | 1/2003 |

(Continued)

OTHER PUBLICATIONS

International Search Report dated Mar. 28, 2008.

(Continued)

*Primary Examiner*—Dung T Nguyen
(74) *Attorney, Agent, or Firm*—McGinn IP Law Group, PLLC

(57) ABSTRACT

A cladding is provided at an outer periphery of a solid-core doped with rare earth ions, and a metal layer is formed to be adjacent to the cladding to provide an optical fiber for a fiber laser device. The metal layer having an inner metal layer and an outer metal layer is disposed along an entire length of the optical fiber for a fiber laser device. An exciting light is incident to the optical fiber for a fiber laser device, and the exciting light is reflection-excited to emit a high power laser oscillation light. A monitoring current is constantly flown into the metal layer. When the disconnection of the optical fiber for a fiber laser device is detected based on the monitoring current, the energization of the optical fiber for a fiber laser device is stopped.

13 Claims, 8 Drawing Sheets

FOREIGN PATENT DOCUMENTS

| | | | |
|---|---|---|---|
| JP | 2004-205764 | | 7/2004 |
| JP | 2006-201299 | * | 8/2006 |
| JP | 2006-572152 | * | 8/2006 |
| WO | 99/57589 | | 11/1999 |
| WO | 2005/013444 | | 2/2005 |

OTHER PUBLICATIONS

Japanese Office Action dated Jul. 1, 2008 with English translation.

* cited by examiner

OPTICAL FIBER FOR FIBER LASER DEVICE AND FIBER LASER DEVICE USING SAME

The present application is based on Japanese Patent Application No. 2006-327359 filed on Dec. 4, 2006, the entire contents of which are incorporated herein by reference.

BACKGROUND OF THE INVENTION

1. Field of the Invention

The present invention relates to an optical fiber for a fiber laser device and a fiber laser device using the same, more particularly, to an optical fiber for a fiber laser device comprising a core and a cladding to transmit a high power laser beam and a fiber laser device using the same.

2. Related Art

It is demanded to develop an inexpensive light source with a high power, for the purpose of a laser beam machining application, a medical application, and the like. As to these requests, a fiber laser and an optical amplifier attract attentions, since it is possible to easily extract a single mode laser beam with a high efficiency by using the fiber laser and the optical amplifier.

FIG. 6 is a schematic block diagram of a general structure of a fiber laser now under development.

A fiber laser device 71 shown in FIG. 6 comprises a semiconductor laser (LD) 72, an exciting light combiner 73 connected to the semiconductor laser 72, an optical fiber 74 for fiber laser, a fiber grating (FBG) 75 formed at an input end of the optical fiber 74, and another fiber grating (FBG) 16 formed an output end of the optical fiber 74.

In the fiber laser device 71 shown in FIG. 6, an exciting light emitted from the semiconductor laser 72 is incident to the input end of the optical fiber 74 via the exciting light combiner 73. The optical fiber 74 for fiber laser is doped with rare earth ions (rare earth element). A plurality of the laser diodes 72 are connected to the optical fiber 74 for fiber laser to obtain a high power.

At the input end of the optical fiber 74 for fiber laser that is doped with the rare earth element, the fiber grating (FBG) 75 that has a transmittance with respect to an exciting light wavelength and a high reflective index with respect to an oscillation light wavelength is formed. At the output end on an opposite side to the input end, another fiber grating (FBG) 76 that partially reflects back the oscillation light is formed. The two fiber gratings (FBG) 75, 76 serve as a total reflection mirror and an output mirror for a laser oscillator to output a laser oscillation light L.

The fiber laser device 71 also functions as an optical amplifier, when the gratings do not form a resonator structure and a signal light having a wavelength coinciding with that of an induced emission light is superimposed on the exciting light to be propagated.

As the optical fiber 74 for fiber laser that is doped with the rare earth ions, a double clad type optical fiber as shown in FIG. 7 is generally used. A core region 77 of the double clad type optical fiber 74 is doped with the rare earth element such as Nd, Yb, Er, Th or the like. A cladding comprises a first cladding region 78 having a refractive index lower than that of the core region 77, and a second cladding region 79 having a refractive index lower than that of the first cladding region 78. Further, a coating layer (not shown) comprising a material generally used in the art or the like is provided at an outer periphery of the second cladding region 79.

An exciting light Le is propagated in multimode through the first cladding region 78 and gradually absorbed by the core region 77 located at a center of the optical fiber 74, so that the exciting light Le is attenuated. According to an end-face excitation type fiber laser using such a double clad structure optical fiber, conversion efficiency from the exciting light Le to a laser oscillation light L is high. The output of the end-face oscillation type fiber laser has been increased year by year, and an oscillation of 10 kW class was also realized.

Further, as conventional optical fibers, JP-T-2002-541507 discloses a photonic crystal fiber and a method for its production, and JP-A-2000-35521 discloses an optical fiber composed of a hollow hole, a cladding having a diffraction grating.

As described above, the fiber laser has a superior beam quality. Further, the output power has bee increased recently. In addition, the realization of the fiber laser with 10 kW class was achieved. Therefore, the development of the fiber laser raises expectation for various processing applications, particularly, application for a laser beam oscillation source for welding or cutting of metallic members. As a problem for putting the high power fiber laser to practical use, there is an issue of safety measures.

In particular, a laser light blocking function in case of fiber disconnection is an essential and indispensable function for the fiber laser device. In the event that the optical fiber is broken, a laser beam having a high energy density may be emitted from a disconnection point, thereby damaging articles around the disconnection point. A system for detecting the disconnection of a fiber laser main body or an optical fiber for fiber laser is generally introduced to avoid such an accident.

To be more concrete, a cable structure incorporating the optical fiber for fiber laser is designed for detecting the disconnection of the fiber laser main body or the optical fiber, instead of designing the fiber laser main body.

For example, FIG. 8 is a schematic diagram of a fiber laser disconnection detection cable 81. In the fiber laser disconnection detection cable 81 as shown in FIG. 8, a metal tape 83 is provided to surround an optical fiber 82 for fiber laser in a cable jacket 84, and an electric current is flown through the metal tape 83. When the optical fiber 82 for fiber laser is disconnected, the laser beam leaks from the optical fiber 82, so that the metal tape 83 will be broken by the leaked laser beam. By detecting the disconnection of the metal tape 83, it is possible to detect the disconnection of the optical fiber 82 for fiber laser.

However, according to this structure, it is necessary to flexibly incorporate the metal tape 83 between the optical fiber 82 for fiber laser and the cable jacket 84. In addition, it is necessary to provide an insulation processing for suppressing a short circuit between the metal tapes 83 even if the metal tapes 83 contact with each other. Accordingly, there is a disadvantage in that manufacturing of such a cable structure is difficult and requires complicated steps.

There are further disadvantages in that a total configuration of the cable is complicated since it is necessary to provide the metal tape 83 at an outer periphery of the optical fiber 82 for fiber laser, and that it is hard to install a fiber laser transmission system cable, since an outer diameter of the cable as well as a weight of the cable are increased.

THE SUMMARY OF THE INVENTION

Accordingly, it is an object of the invention to provide an optical fiber for a fiber laser device in which an optical fiber itself is provided with a disconnection detecting function.

Further, it is another object of the invention to provide a fiber laser device, by which it is possible to stop a laser oscillation immediately in case of the optical fiber disconnection by using the optical fiber for a fiber laser device.

According to a first feature of the invention, an optical fiber for a fiber laser device, for transmitting a high power laser beam, comprises:

a solid-core;

a cladding; and a metal layer comprising an inner metal layer and an outer metal layer, and the metal layer being formed to be adjacent to the cladding along an entire length of the optical fiber.

In the optical fiber for a fiber laser device, the solid-core may be doped with a rare earth ion to emit a light by a predetermined excitation, and functions as a laser oscillation medium by reflection excitation of the emitted light.

In the optical fiber for a fiber laser device, it is preferable that one of the inner metal layer and the outer metal layer comprises a metal having a high adhesion property with the cladding and a film thickness of 1 to 3 μm and another of the inner metal layer and the outer metal layer comprises a metal having a high electrical conductivity and a film thickness of 5 to 15 μm.

The optical fiber for a fiber laser device may further comprise an insulative coating layer as an outermost layer.

In the optical fiber for a fiber laser device, the insulative coating layer may comprise a polyimide resin.

In the optical fiber for a fiber laser device, the cladding may comprise a first cladding layer including a plurality of air holes and a second cladding layer provided at an outer periphery of the first cladding layer.

In the optical fiber for a fiber laser device, the cladding may further comprise an air hole layer comprising a plurality of air holes arranged in a hexagonal structure between the first cladding layer and the second cladding layer.

In the optical fiber for a fiber laser device, the metal layer is provided at an outer periphery of the cladding.

According to a second feature of the invention, a fiber laser device comprises:

an optical fiber for a fiber laser device for transmitting a high power laser beam including a solid-core, a cladding, and a metal layer formed to be adjacent to the cladding along an entire length of the optical fiber, to which an exciting light is input and reflection-excited to output a laser oscillation light;

an energizing unit for constantly energizing the optical fiber for a fiber laser device; and a monitoring unit for monitoring an energization state of the optical fiber for a fiber laser device.

The fiber laser device may further comprise:

a blocking unit for blocking the exciting light when the energization of the optical fiber laser for a fiber laser device is blocked.

Effects of the Invention

According to the present invention, it is possible to provide an optical fiber for fiber laser device in which an optical fiber itself is provided with a disconnection detecting function.

BRIEF DESCRIPTION OF THE DRAWINGS

Next, the present invention will be explained in more detail in conjunction with appended drawings, wherein.

DESCRIPTION OF THE PREFERRED EMBODIMENTS

Next, preferred embodiments according to the present invention will be explained in more detail in conjunction with the appended drawings.

First Preferred Embodiment

Structure of a Metal Coated Optical Fiber for Fiber Laser

Figure 1:
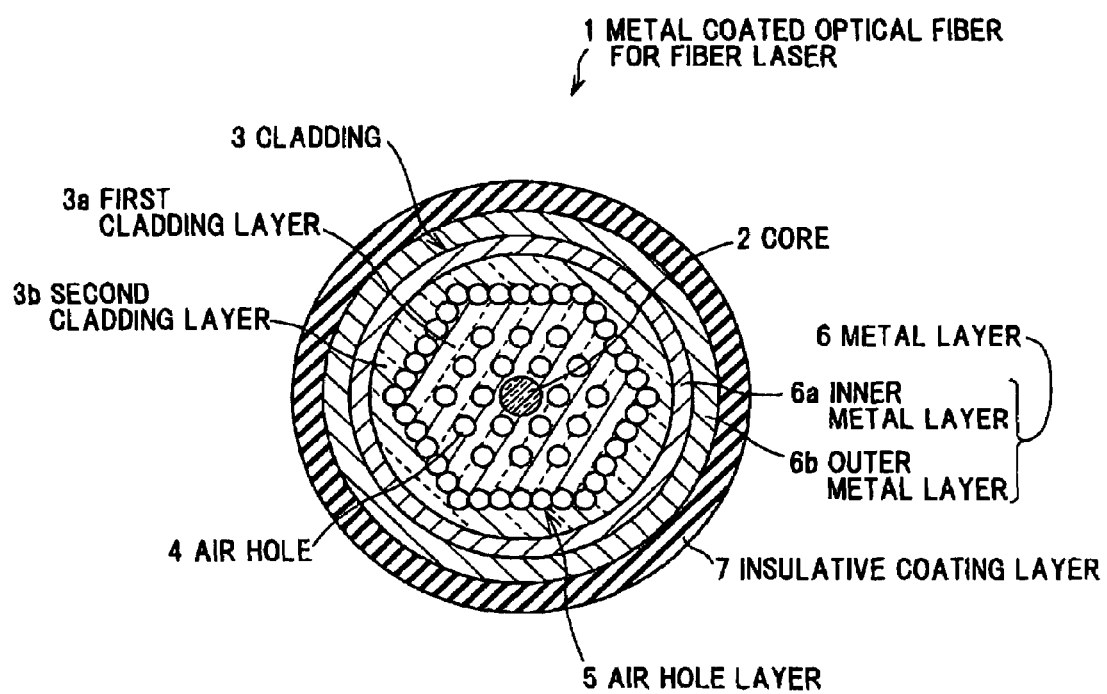
FIG. 1 is a lateral cross-sectional view of an optical fiber for a fiber laser device (a metal coated optical fiber for fiber laser) in a first preferred embodiment according to the present invention.

FIG. 1 is a lateral cross-sectional view of an optical fiber for a fiber laser device (a metal coated optical fiber for fiber laser) in a first preferred embodiment according to the present invention.

As shown in FIG. 1, a metal coated optical fiber 1 for fiber laser as an optical fiber for a fiber laser device in the first preferred embodiment comprises a solid-core 2 and a cladding 3, which is an optical fiber to transmit a laser beam with a high power. The core 2 comprises a pure quartz doped with rare earth ions such as Nd, Yb, Er, Th and the like.

The metal coated optical fiber 1 for fiber laser has a light emitting function to emit a light by a predetermined oscillation, since the core 2 is doped with the rare earth ions. As discussed below referring to FIG. 5, the metal coated optical fiber 1 for fiber laser also functions as a laser oscillation medium by reflection exciting the emitted light.

The cladding 3 comprises a first core cladding part (first cladding layer) 3a that is formed at a periphery of the core 2 and has a refractive index effectively lower than that of the core 2, and a second cladding part (second cladding layer) 3b formed at an outer periphery of the first cladding part 3a. For example, each of the first and the second cladding part 3a, 3b comprises pure quartz doped with F.

A plurality of air holes 4 having a refractive index of 1 are formed to have a dissemination-shape (or honeycomb shape) in a lateral cross sectional view around the core 2 in the first cladding part 3a along a length (an entire length) of the core 2, so as to lower an effective refractive index of the first cladding part 3a than that of the core 2.

At an interface between the first cladding part 3a and the second cladding part 3b, an air hole layer 5, in which a plurality of the air holes 4 are arranged in a hexagonal shape in a lateral cross sectional view, is formed, so as to effectively confine an exciting light (pumping light) which excites the rare earth ions doped to the core 2 to emit the light in the cladding part 3a.

As a part adjacent to the cladding 3, a metal layer 6 is formed at an outer periphery of the second cladding part 3b. This metal layer 6 comprises an inner metal layer 6a and an outer metal layer 6b. An insulative coating layer 7 is formed at an outer periphery of the second cladding part 3b.

(Structure of the Metal Layer)

The inner metal layer 6a comprises a metal having a high adhesion property with the cladding 3 such as Ni and a film thickness of 1 to 3 μm. The outer metal layer 6b comprises a metal having a high electric conductivity such as Au, Pt, Cu, Ag, and a film thickness of 5 to 15 μm.

In other words, as a material of the metal layer 6, Au, Pt, Ni, Cu, Ag or the like may be applied. The metal layer 6 has a multi-layered structure in that the metals such as Au, Pt, Ni, Cu, Ag or the like are laminated by plating. An electroless plating is provided on a quartz fiber, a Ni plating is provided on the metal coating formed directly above the quartz fiber, and a metal plating such as Au, Pt, Cu, Ag is provided thereon. Further, in consideration of deterioration of the metal due to an influence of oxidation or the like, it is preferable to provide Au or Pt on the Ni plating.

Further, in the metal layer 6, there is a disadvantage in a strength assurance of the quartz fiber, when a film thickness of a metal coating on the Ni plating is less than 5 μm. On the other hand, when the film thickness of the metal coating on the Ni plating is greater than 15 μm, a metal rigidity of the metal layer 6 is too strengthened, so that it is difficult to bend the metal coated optical fiber 1 for fiber laser. Further, a material cost is increased. Therefore, the film thickness of the metal coating (i.e. the outer metal layer 6b) on the Ni plating is preferably 5 to 15 μm.

This metal layer 6 will be explained below in more detail.

The metal layer 6 is provided along an entire length of the metal coated optical fiber 1 for fiber laser to have a circular lateral cross section. As a coating metal material, Au is most preferable, since Au has a high malleability without being corroded or oxidized. However, it is necessary to use a sputtering method to directly coat Au on the second cladding part 3b, so that it is difficult to fabricate a lengthy optical fiber.

Therefore, the Ni layer that can be provided by electroless plating on a surface of the quartz glass is provided as a first layer (inner metal layer 6a), and Au layer is provided by electrolysis plating as a second layer (outer metal layer 6b) by utilizing a electric conductivity provided by a formation of the Ni layer.

Herein, a film thickness of the Ni layer by the electroless plating is preferably 1 to 3 μm. The reason that the Ni layer with the film thickness of not less than 1 μm is required will be explained as follows. In a subsequent step for providing the Au electrolysis plating, an Au plating layer is formed by energizing the Ni layer. In concrete, the Au layer is formed by soaking the quartz fiber coated by the Ni layer in a gold potassium cyanide solution. Therefore, when the film thickness of the Ni layer is less than 1 μm, the Ni plated optical fiber may be broken and disconnected at a contact with the electrode.

The reason that the Ni layer having the film thickness of not greater than 3 μm is required will be explained as follows. Stabilization of the Ni plating formed by the electroless plating is difficult. According to the experiment of the Inventors of the present invention, when the film thickness of the Ni plating layer is increased to be greater than 3 μm, a frequency of exfoliations of the Ni plating layer due to cracking will be increased, so that a production yield will be significantly decreased. It is also possible to increase the film thickness of the Ni plating layer, by further providing the electrolysis plating of Ni. However, since the Ni layer is easily oxidized and the oxidized Ni layer is fragile and easily exfoliated. Accordingly, the Au layer that is hardly oxidized is plated by the electrolysis plating on the Ni layer.

The reason for using the plating method for forming the metal layer 6 will be explained as follows. It is possible to coat (deposit) most metal on a surface of the quartz by using the sputtering method. However, the manufacturing cost is increased and it is difficult to increase the film thickness of the metal layer, and increase the length of the optical fiber, so that the use of the sputtering is not realistic.

In this preferred embodiment, the film thickness of the Au layer is set to be 5 μm. In the case that a total film thickness of the Ni layer and the Au layer is small, when a current (monitoring current described below) is flown in the metal layer 6, a film quality is deteriorated by a self-heating due to a electric resistance (i.e. the metal layer is deteriorated by the heat), and the metal layer may be finally disconnected.

(Relationship Between a Metal Layer Film Thickness and a Disconnection Time)

Figure 2:
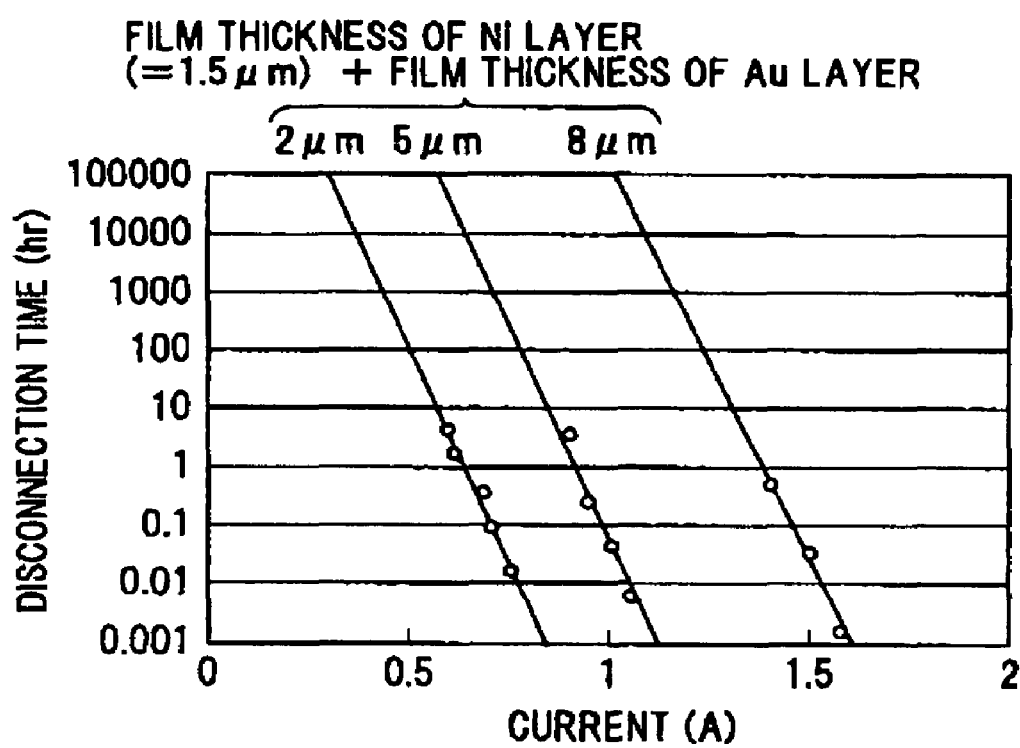
FIG. 2 is a graph showing a dependency to a metal layer film thickness of a disconnection time caused by energization of the metal coated optical fiber for fiber laser shown in FIG. 1.

FIG. 2 is a graph showing a dependency to a metal layer film thickness of a disconnection time due to energization of the metal coated optical fiber for fiber laser shown in FIG. 1. FIG. 2 shows an experimental result of the current and the fiber disconnection time when a current of about 0.6 to 1.6 A that is sufficient as the monitoring current is flown in the metal layer 6 of the metal coated optical fiber 1 for fiber laser (a diameter of a glass fiber part, i.e. an outer diameter of the second cladding part 3b is 125 μm), in which the Au layer having a film thickness of 2, 5, or 8 μm is provided on the Ni layer having a film thickness of 1.5 μm. It is concluded that the optical fiber 1 will not be disconnected even though the current of about 0.6 A is flown for 100,000 hours if the Au film thickness is not less than 5 μm from the experimental result shown in FIG. 2.

(Structure of Insulative Coating Layer)

As an outermost layer that is an outer periphery of the second cladding part 3b, the insulative coating layer 7 is formed. As the insulative coating layer 7, a layer comprising a polyimide resin with a heat resistance and insulation property is employed.

Figure 3A:
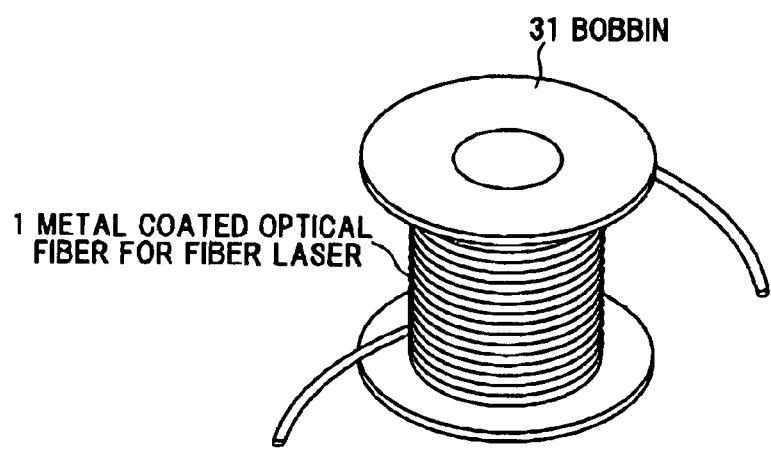
FIGS. 3A and 3B are explanatory diagrams showing states that the metal coated optical fiber for fiber laser shown in FIG. 1 is accommodated.
Figure 3B:
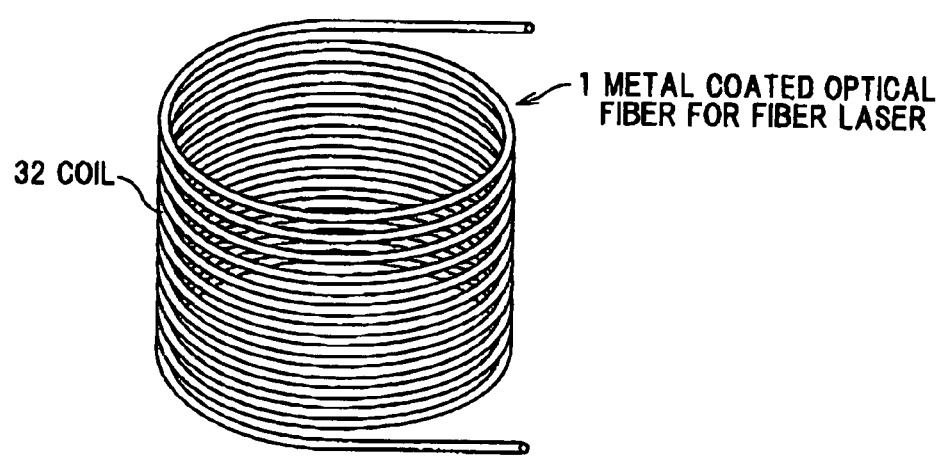

The metal coated optical fiber 1 for fiber laser is usually held in a state of being wound around a bobbin 31 as shown in FIG. 3A, or held as a coil 32 without using the bobbin as shown in FIG. 3B.

At this time, if the metal layers 6 of the optical fiber 1 to be energized are in contact with each other, an electrical short-circuit will occur. As a result, it is impossible to conduct the fiber disconnection monitoring by the energization. Further, the metal layers of the optical fiber may be damaged by the heat generated from sparks caused by the short circuit. In the worst case, the disconnection may be caused.

Accordingly, it is preferable that the insulative coating layer 7 is formed as the outermost layer at the outer periphery of the metal layer 6, so as to suppress the short circuit even when the optical fibers 1 are in contact with each other. It is expected that a high power laser beam is oscillated or transmitted so that a part of energy of the laser beam is converted into the heat, thereby elevating a temperature of the fiber main body (a portion inside the metal layer 6). Particularly in a high power system, it is effective to provide a resin (e.g. polyimide resin) with an excellent heat resistance and insulation property on the metal layer 6, to provide the insulative coating layer 7.

As the insulative coating layer 7, it is possible to use an ultraviolet (UV) curable resin or a heat curable silicone resin that is generally used in the optical fiber. The insulation property of these resins is generally good.

In other words, by forming the insulative coating layer on the metal layer 6, it is possible to keep the electrical insulation at a contact point of the optical fibers 1, when the metal coated optical fiber 1 for fiber laser is stored by being wound or stored in the coil, by forming insulative coating layer 7 on metal layer 6.

In this preferred embodiment, the Ni layer with a film thickness of 1.5 μm that is formed by the electroless plating is provided as the inner metal layer 6a on the second cladding part 3b, the Au layer with a film thickness of 8 μm that is formed by the electrolysis plating is provided as the outer metal layer 6b at the outer periphery of the Ni layer, and the insulative coating layer 7 comprising the polyimide resin with the excellent heat resistance with a film thickness of 15 μm is coated as the outermost layer. An outer diameter of the metal coated optical fiber 1 for fiber laser is approximately the same as an outer diameter of an optical fiber for fiber laser generally used.

Second Preferred Embodiment

Optical Fiber for Fiber Laser Transmission

Figure 4:
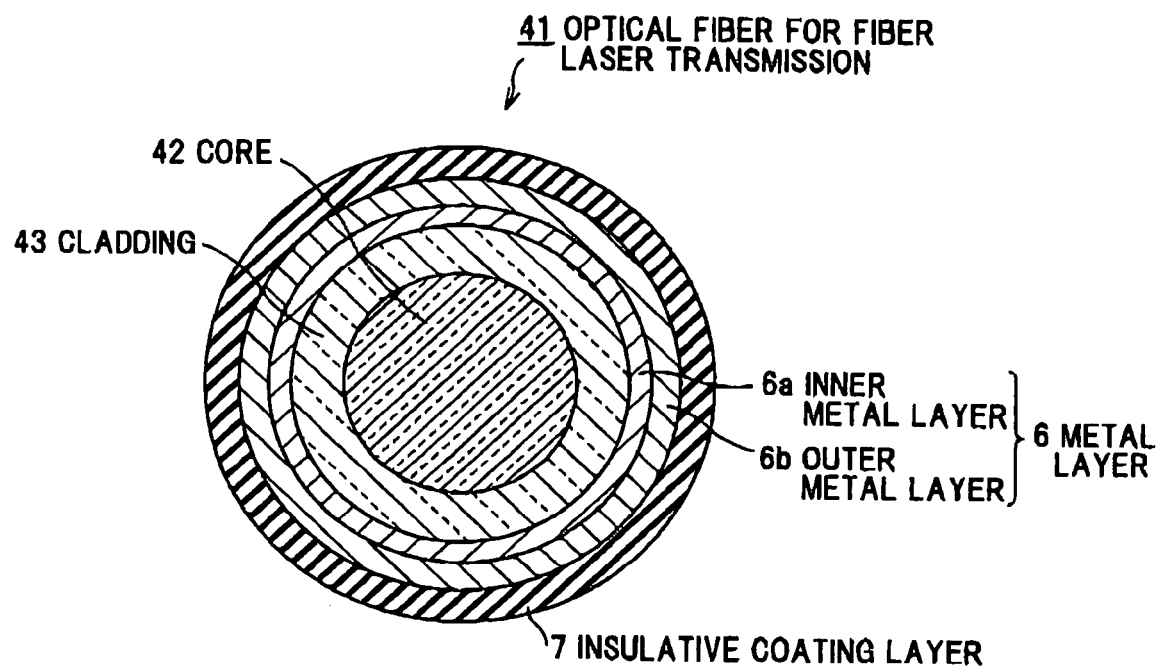
FIG. 4 is a cross sectional view of an optical fiber for a fiber laser device (an optical fiber for fiber laser transmission) in a second embodiment according to the present invention.

FIG. 4 is a cross sectional view of an optical fiber for a fiber laser device (an optical fiber for fiber laser transmission) in a second embodiment according to the present invention.

As shown in FIG. 4, an optical fiber 41 for fiber laser transmission comprises a solid-core 42 comprising a pure quartz, a cladding 43 comprising a pure quartz doped with F and provided at an outer periphery of the core 42, a metal layer 6 provided at an outer periphery of the cladding 43 similarly to the metal layer 6 in FIG. 1, and an insulative coating layer 7 as an outermost layer.

In this preferred embodiment, a diameter of the core 42 is 400 μm, and an outer diameter of the cladding 43 is 600 μm. The outer diameters of the metal layer 6 and the insulative coating layer 7 are same as those of the metal coated optical fiber 1 for fiber laser shown in FIG. 1.

Third Preferred Embodiment

Fiber Laser Device Using the Metal Coated Optical Fiber for Fiber Laser

Next, a fiber laser device using the metal coated optical fiber 1 for fiber laser in the first preferred embodiment will be explained in conjunction with FIG. 5.

Figure 5:
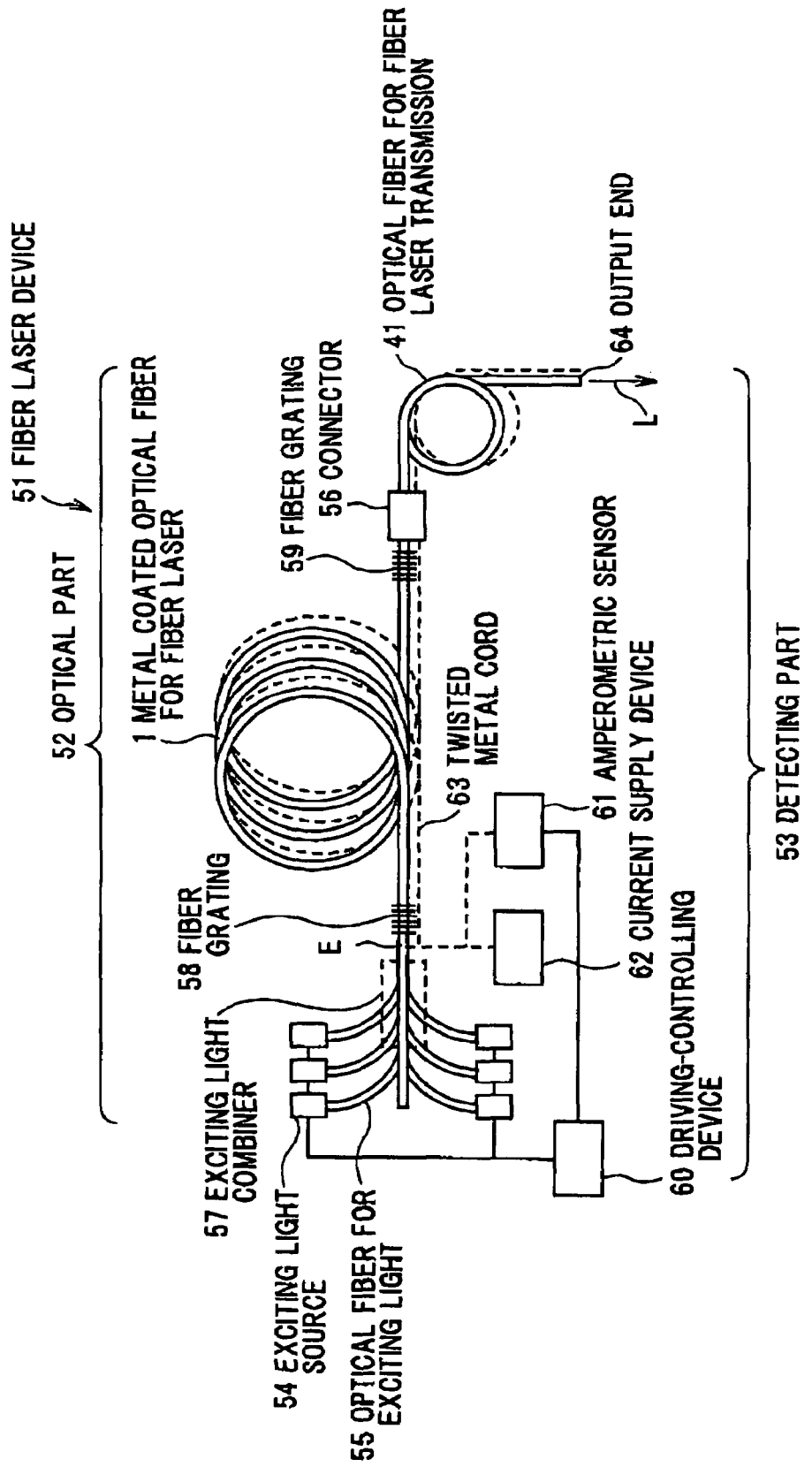
FIG. 5 is a schematic diagram of a fiber laser device in a third preferred embodiment.
Figure 6:
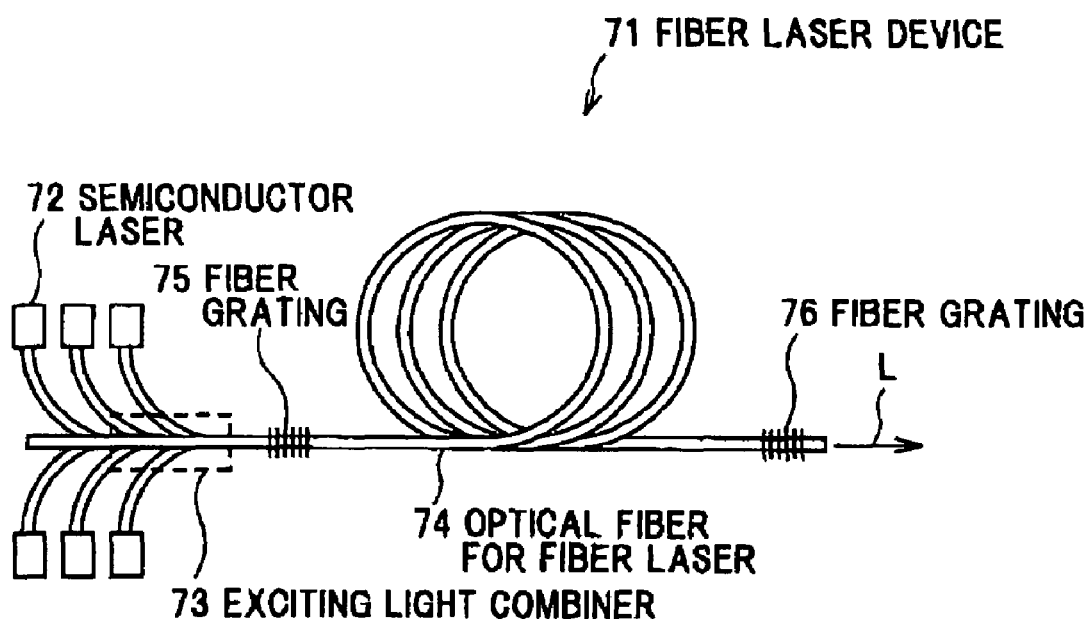
FIG. 6 is a schematic diagram of a conventional fiber laser device.
Figure 7:
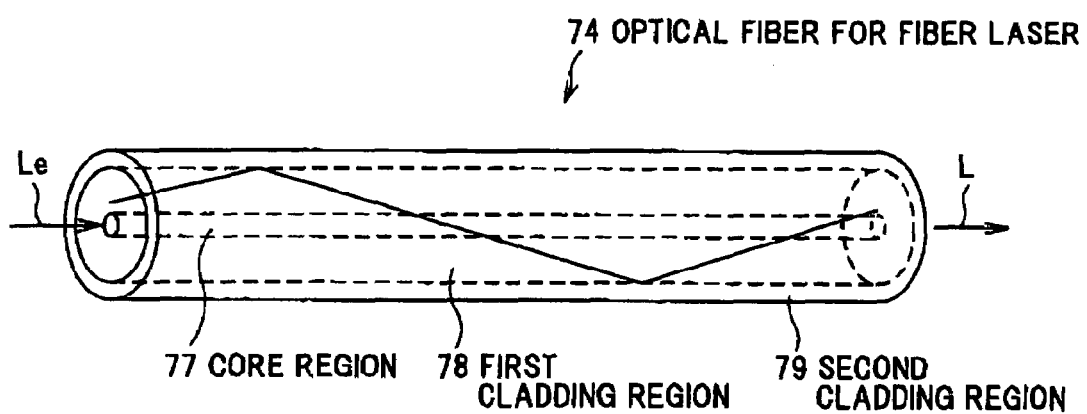
FIG. 7 is a schematic diagram of a conventional double clad type optical fiber for fiber laser.

As shown in FIG. 5, a fiber laser device 51 in this preferred embodiment mainly 6 comprises an optical part 52 to output a laser oscillation light L and a detecting part 53 to detect a disconnection of an optical fiber constituting the optical part 52.

(Structure of the Optical Part)

The optical part 52 comprises a plurality of exciting light sources 54 for obtaining an exciting light with a high power, a plurality of optical fibers 55 for exciting light respectively connected to the exciting light sources 54, a metal coated optical fiber 1 for fiber laser bundled up together with the optical fibers 55 for exciting light, that has a light emitting function to emit the light by a predetermined excitation and serves as a laser oscillation medium by reflection excitation of the emitted light, an optical fiber 41 for fiber laser transmission that is connected to the metal coated optical fiber 1 for fiber laser to transmit the laser oscillation light L, and a connector 56 to connect the optical fiber 41 for fiber laser transmission with the metal coated optical fiber 1 for fiber laser.

As the exciting light source 54, a laser diode (LD) is used. The metal coated optical fiber 1 for fiber laser and the optical fibers 55 for exciting light are bundled up to provide an exciting light combiner 57.

At an input end (a downstream end with respect to the exciting light combiner 57) of the metal coated optical fiber 1 for fiber laser, to which the laser oscillation light L is incident, a fiber grating (FBG) 58 that has a transmittance with respect to the exciting light wavelength and has a high reflective index with respect to the oscillation light wavelength is formed. At an output end (an upstream end with respect to the connector 56) of the metal coated optical fiber 1 for fiber laser, from which the laser oscillation light L is output, another fiber grating (FBG) 59 that partially reflects the exciting light and has a grating space different from that of the fiber grating 58 is formed. The two fiber gratings 58, 59 serve as a total reflection mirror and an output mirror of a laser resonator. The fiber gratings 58, 59 are formed prior to the formation of the metal layer 6 in FIG. 1.

The metal layer 6 is not formed at a part, in which the exciting light combiner 57 is formed in the metal coated optical fiber 1 for fiber laser. Alternatively, the metal layer formed at the part, in which the exciting light combiner 57 is formed in the metal coated optical fiber 1 for fiber laser is exfoliated.

The optical fiber 41 for fiber laser transmission which transmits the laser oscillation light L is connected to the output end of the metal coated optical fiber 1 for fiber laser via the connector 56.

(Structure of the Detecting Part)

The detecting part 53 comprises a driving-controlling device 60 connected to all of the exciting light sources 54 for driving the exciting light sources 54, an amperometric sensor 61 connected to the driving-controlling device 60 for measuring a monitoring current (sensing current) flown into the metal layer 6 of the metal coated optical fiber 1 for fiber laser as a current sensor, a current supply device 62 for supplying the sensing current to the metal layer 6 as an energizing means (energizing apparatus) for a constant energization, and a twisted metal cord 63 provided along the metal coated optical fiber 1 for fiber laser and the optical fiber 41 for fiber laser transmission for connecting the amperometric sensor 61 and the current supply device 62.

The driving-controlling device 60 comprises a monitoring means for monitoring an energizing state of the metal coated optical fiber 1 for fiber laser based on a measured value of the sensing current measured by the amperometric sensor, and a blocking (cut-off) means for blocking the exciting light when the energization of the metal coated optical fiber 1 for fiber laser is blocked.

As the current supply device 62, both a direct current source and an alternating current source may be used, and an output power may be weak. It is preferable to use the current of about 1 A as the sensing current, since the current greater than 10 A uses a useless energy in terms of energy conservation, and it is difficult to control an extremely weak current.

In other words, it is enough to provide the sensing current for monitoring the energization of the metal layer 6 that is used in a commercial circuit tester. However, it is preferable to provide a mechanism for outputting the energization state as a simple electrical signal, since the output signal can be used as a monitoring signal for controlling the exciting light.

The connection between the optical part 52 and the detecting part 53 is conducted by electrically connecting the twisted metal cord 63 with the metal layer 6 at an exciting light input part E that is located between the exciting light combiner 57 of the metal coated optical fiber 1 for fiber laser and the FBG 58.

One end of the twisted metal cord 63 is connected to the amperometric sensor 61, the current supply device 62, and the exciting light input part E respectively, and electrically connected and extended by the connector 56, and another end is connected to an output end 64 of the optical fiber 41 for fiber laser transmission.

According to this structure, an electric circuit section is defined in the fiber laser device 51, in that the current supplied from an output terminal of the current supply device 62 is frown into the twisted metal cord 63, the metal layer 6 of the metal coated optical fiber 1 for fiber laser, and the metal layer 6 of the optical fiber 41 for fiber laser transmission, and is returned back to the output end 64 to reach the twisted metal cord 63 and an input terminal of the current supply device 62.

(Operation of the Fiber Laser Device 51)

An effect of the first preferred embodiment will be explained together with the operation of the fiber laser device 51.

When each of the exciting light sources 52 are driven by the driving-controlling device 60, the exciting light is emitted from each of the exciting light sources 52, and the emitted light is incident to the metal coated optical fiber 1 for fiber laser via the exciting light combiner 57 and the exciting light input part E.

The exciting light incident to the metal coated optical fiber 1 for fiber laser is amplified inside of the metal coated optical fiber 1 for fiber laser, and the FBGs 58, 59 function as the total reflection mirror and the output mirror of the laser resonator, so that the laser oscillation light L is generated, and output from the output end 64 of the optical fiber 41 for fiber laser transmission.

At the time of the laser oscillation, the driving-controlling device 60 of the fiber laser device 51 controls the current supply device 62, to always (constantly) flow the current into the metal coated optical fiber 1 for fiber laser, and flow a determined sensing current to the metal layer 6 of the metal coated optical fiber 1 for fiber laser. The sensing current is flown through the aforementioned electric circuit and returned back to the current supply device 62, and the value of the sensing current returned to the current supply device 62 is measured by the amperometric sensor 61 to be fed back to the driving-controlling device 60.

The driving-controlling device 60 monitors the energization state of the metal coated optical fiber 1 for fiber laser based on the measured value of the sensing current, to determine a presence of the disconnection of the metal coated optical fiber 1 for fiber laser.

In more detail, the driving-controlling device 60 determines that the metal coated optical fiber 1 for fiber laser is in a sound state (normal state) without the disconnection when the measured value of the sensing current exceeds a predetermined threshold level, and continues the operation of the fiber laser device 51.

On the other hand, the driving-controlling device 60 determines that the metal coated optical fiber 1 for fiber laser is in an extraordinary state (abnormal state) where the metal coated optical fiber 1 for fiber laser is disconnected or the metal layer 6 is damaged or deteriorated, when the measured value of the sensing current is lower than the predetermined threshold level.

At the extraordinary state, the driving-controlling device 60 stops the current supply device 62, to block the energization of the metal coated optical fiber 1 for fiber laser and to block the energization of the exciting light sources 54 simultaneously, so as to stop the operation of the exciting light sources 54, thereby stopping the input of the exciting light to the metal coated optical fiber 1 for fiber laser. As a result, the driving-controlling device 60 stops the operation of the fiber laser device 51.

In the fiber laser device 51, the optical fiber 41 for fiber laser transmission is connected to the metal coated optical fiber 1 for fiber laser via the connector 56, so that the sensing current is flown through the metal layer 6 of the optical fiber 41 for fiber laser transmission. Similarly to the above operation, it is possible to monitor the energization state of the optical fiber 41 for fiber laser transmission to determine the presence of the disconnection of the optical fiber 41 for fiber laser transmission.

As described above, in the fiber laser device 51, the metal coated optical fiber 1 for fiber laser and the optical fiber 41 for fiber laser transmission constitute the optical part 52, and the detecting part 53 is connected to the optical part 52. The energization of the optical fibers per se is conducted.

Accordingly, in the fiber laser device 51, it is possible to determine the abnormal state of either the metal coated optical fiber 1 for fiber laser or the optical fiber 41 for fiber laser transmission, by monitoring the sensing current flown into the metal layers 6 of the both optical fibers 1, 41.

Further, in the fiber laser device 51, the laser oscillation is immediately stopped by the driving-controlling device 60 composing the detecting part 53 in the abnormal state of the optical fiber 1 or 41, thereby assuring the security of the fiber laser device 51.

Still further, since the metal coated optical fiber 1 for fiber laser in the first preferred embodiment and the optical fiber 41 for fiber laser transmission in the second preferred embodiment basically have simple structures provided with the metal layers 6 respectively, and the structure of the detecting part 53 is also simple, it is possible to construe a security system of the fiber laser device 51 easily and inexpensively.

In other words, according to the fiber laser device 51 in this preferred embodiment, the metal layers 6 of the optical fibers 1, 41 are always (constantly) energized, and the soundness of the optical fibers 1, 41 (the state of no disconnection or the state of the disconnection) can be determined by monitoring the energization state. In the abnormal state, it is possible to stop the operation of the fiber laser device 51 by stopping the exciting light sources 54, thereby assuring the security of the fiber laser device 51.

In the metal coated optical fiber 1 for fiber laser, the thin metal layer 6 is formed at the outer periphery of the second cladding part 3*b* that is one of parts adjacent to the cladding 3, and the optical fiber 1 per se is provided with the metal layer 6 for the disconnection detection. Therefore, the metal coated optical fiber 1 for fiber laser is an optical fiber for fiber laser in which the optical fiber per se is provided with the disconnection detecting function.

Figure 8:
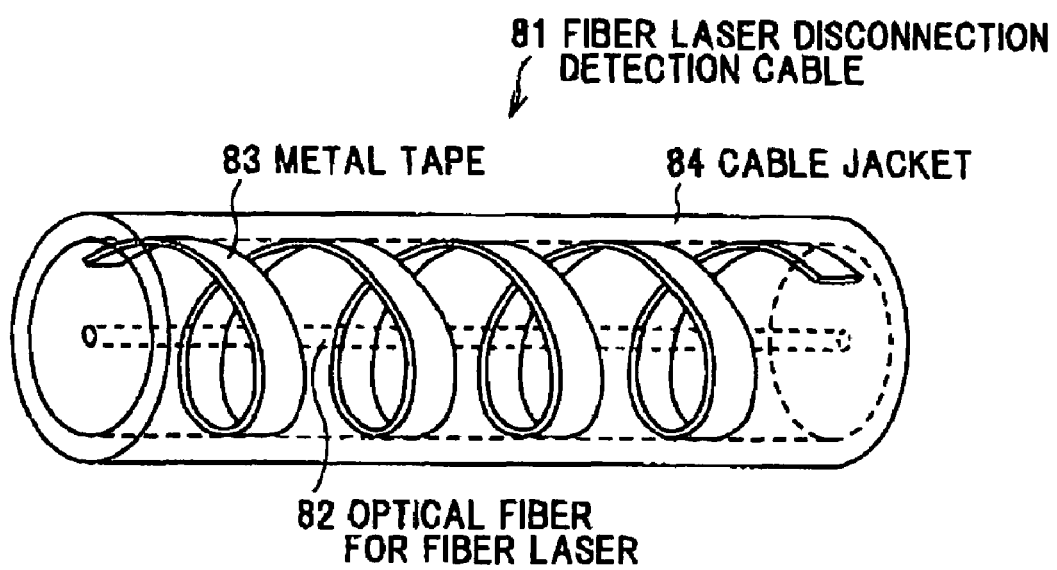
FIG. 8 is a schematic diagram of an example of a structure of a conventional fiber laser disconnection detection cable.

As described above, according to the metal coated optical fiber 1 for fiber laser, it is possible to reduce the diameter and the weight of the cable per se, to obtain the flexibility of the cable, and to realize a flexible cable with low cost, compared with the conventional fiber laser disconnection detection cable 81 of FIG. 8.

Next, a detailed ground for reducing the diameter and the weight of the cable will be explained below.

In the conventional fiber laser disconnection detection cable 81, it is necessary to dispose the metal tape 83 with the insulative coating spirally around the outer periphery of the optical fiber 82. The reason for spirally providing the metal tape 83 is to provide the cable 81 with the flexibility.

In the case that the metal tape 83 is wound directly around the optical fiber 82 for fiber laser, when the cable 81 is bent, a lateral pressure from the optical fiber 82 may be applied to the metal tape 83 for fiber laser, thereby affecting on an optical transmission characteristic. In addition, the cable jacket 84 may be damaged so that the optical fiber 82 for fiber laser may be disconnected. Accordingly, a space is required between the spiral metal tape 83 and the optical fiber 82 for fiber laser, and it is necessary to hold a configuration of the space.

For satisfying the above requirements, it is necessary to redesign the cable configuration, and to increase the outer diameter of the cable 81 for obtaining the space. In accordance with the increase in the outer diameter of the cable, a bending rigidity is increased, so that it is hard to bend the cable, and a bending radius is increased, thereby deteriorating the flexible characteristic.

On the contrary, the metal coated optical fiber 1 for fiber laser in the first preferred embodiment and the optical fiber 41 for fiber laser transmission in the second preferred embodiment have the configurations approximately same as the configuration (particularly the diameter) of the generally used optical fiber, and have the energization function. Therefore, it is possible to design the cable configurations with the convenience same as that of the optical fiber.

In addition, it is possible to flow the disconnection sensing current into the metal coated optical fiber 1 for fiber laser when used in the fiber laser device 51. In addition, it is possible to confine the high power exciting light and the laser oscillation light within the metal layer 6. The function and effect of the metal coated optical fiber 1 for fiber laser are similar to those of the optical fiber 41 for fiber laser transmission.

Concerning the metal coated optical fiber 1 for fiber laser in the preferred embodiments, an example of forming the thin metal layer 6 at the outer periphery of the second cladding part 3b as one of the parts adjacent to the cladding 3 is explained. However, as the part adjacent to the cladding 3, a metal layer with a double layered structure similar to the metal layer 6 may be formed in one of the air holes 4. For this case, an outer coating layer comprises a metal having a high adhesion property with the cladding 3, and an inner coating layer comprises a metal with high electrical conductivity.

Although the invention has been described with respect to the specific embodiments for complete and clear disclosure, the appended claims are not to be thus limited but are to be construed as embodying all modifications and alternative constructions that may occur to one skilled in the art which fairly fall within the basic teaching herein set forth.

What is claimed is:

1. An optical fiber for a fiber laser device, for transmitting a high power laser beam, comprising:
    a solid-core;
    a cladding; and
    a metal layer comprising an inner metal layer and an outer metal layer, and the metal layer being formed to be adjacent to the cladding along an entire length of the optical fiber,
    wherein one of the inner metal layer and the outer metal layer comprises a metal having a high adhesion property with the cladding and a film thickness of 1 to 3 μm and another of the inner metal layer and the outer metal layer comprises a metal having a high electrical conductivity and a film thickness of 5 to 15 μm.

2. The optical fiber for a fiber laser device according to claim 1, wherein the solid-core is doped with a rare earth ion to emit a light by a predetermined excitation, and functions as a laser oscillation medium by reflection excitation of the emitted light.

3. The optical fiber for a fiber laser device according to claim 1, further comprising an insulative coating layer as an outermost layer.

4. The optical fiber for a fiber laser device according to claim 3, wherein the insulative coating layer comprises a polyimide resin.

5. The optical fiber for a fiber laser device according to claim 1, wherein the cladding comprises a first cladding layer including a plurality of air holes and a second cladding layer provided at an outer periphery of the first cladding layer.

6. The optical fiber for a fiber laser device according to claim 1, wherein the cladding comprises an air hole layer comprising a plurality of air holes arranged in a hexagonal structure.

7. The optical fiber for a fiber laser device according to claim 1, wherein the metal layer is provided at an outer periphery of the cladding.

8. An optical fiber for a fiber laser device, for transmitting a high power laser beam, comprising:
    a solid-core;
    a cladding; and
    a metal layer comprising an inner metal layer and an outer metal layer, and the metal layer being formed to be adjacent to the cladding along an entire length of the optical fiber,
    wherein the cladding comprises an air hole layer comprising a plurality of air holes arranged in a hexagonal structure.

9. The optical fiber for a fiber laser device according to claim 8, wherein the solid-core is doped with a rare earth ion to emit a light by a predetermined excitation, and functions as a laser oscillation medium by reflection excitation of the emitted light.

10. The optical fiber for a fiber laser device according to claim 8, further comprising an insulative coating layer as an outermost layer.

11. The optical fiber for a fiber laser device according to claim 10, wherein the insulative coating layer comprises a polyimide resin.

12. The optical fiber for a fiber laser device according to claim 8, wherein the cladding comprises a first cladding layer including a plurality of air holes and a second cladding layer provided at an outer periphery of the first cladding layer.

13. The optical fiber for a fiber laser device according to claim 8, wherein the metal layer is provided at an outer periphery of the cladding.

* * * * *